(12) United States Patent
Hollenborg et al.

(10) Patent No.: US 12,274,572 B2
(45) Date of Patent: Apr. 15, 2025

(54) MOBILE MEDICAL DEVICE INCLUDING A LIDAR SENSOR AND A METHOD FOR CONTROLLING SUCH A MOBILE MEDICAL DEVICE

(71) Applicant: Siemens Healthcare GmbH, Erlangen (DE)

(72) Inventors: Ingo Hollenborg, Bayreuth (DE); Martin Ossa Kafentzis, Heroldsberg (DE); Markus Weiten, Nuremberg (DE); Alexander Gemmel, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 260 days.

(21) Appl. No.: 17/950,382

(22) Filed: Sep. 22, 2022

(65) Prior Publication Data

US 2023/0095366 A1 Mar. 30, 2023

(30) Foreign Application Priority Data

Sep. 27, 2021 (DE) ..................... 10 2021 210 771.0

(51) Int. Cl.
*A61B 6/00* (2024.01)
*A61B 6/10* (2006.01)
(Continued)

(52) U.S. Cl.
CPC ............ *A61B 6/4405* (2013.01); *A61B 6/102* (2013.01); *A61B 6/4441* (2013.01);
(Continued)

(58) Field of Classification Search
CPC ......... A61B 6/032; A61B 6/035; A61B 6/102; A61B 6/44; A61B 6/4405; A61B 6/4411;
(Continued)

(56) References Cited

U.S. PATENT DOCUMENTS

| 8,050,863 B2 * | 11/2011 | Trepagnier | B60W 30/00 340/436 |
| 8,139,109 B2 * | 3/2012 | Schmiedel | H04N 13/243 348/148 |

(Continued)

FOREIGN PATENT DOCUMENTS

| DE | 102008046345 A1 | 3/2010 |
| DE | 102015218922 A1 | 3/2017 |

(Continued)

*Primary Examiner* — Allen C. Ho
(74) *Attorney, Agent, or Firm* — Lempia Summerfield Katz LLC (57) ABSTRACT

A method is provided for the automatic control of a drivable, mobile medical device having a collision control system that has at least one LiDAR sensor. The method includes: locomotion of the device at a first speed, periodic joint scanning of at least one part of the surroundings of the device; using the at least one LiDAR sensor during the locomotion of the device; evaluating the scan data of the surroundings that has been recorded by the LiDAR sensor; and evaluating the scan data of the specified device section, the scan data being recorded by the LiDAR sensor in such a manner that a functional capability of the LiDAR sensor is tested and the speed of the device is controlled in a closed-loop manner depending on the result of the evaluations.

17 Claims, 4 Drawing Sheets

(51) Int. Cl.
*B60W 30/09* (2012.01)
*B60W 30/095* (2012.01)
*G01S 17/42* (2006.01)
*G01S 17/93* (2020.01)
*G01S 17/931* (2020.01)

(52) U.S. Cl.
CPC .......... *A61B 6/4476* (2013.01); *B60W 30/09* (2013.01); *B60W 30/095* (2013.01); *B60W 30/0956* (2013.01); *G01S 17/42* (2013.01); *G01S 17/93* (2013.01); *G01S 17/931* (2020.01)

(58) Field of Classification Search
CPC ... A61B 6/4429; A61B 6/4435; A61B 6/4441; A61B 6/4447; A61B 6/4476; A61B 6/4482; B60W 30/09; B60W 30/095; B60W 30/0953; B60W 30/0956; G01S 17/93; G01S 17/931
USPC .................................. 378/91, 196–198, 207
See application file for complete search history.

(56) References Cited

U.S. PATENT DOCUMENTS

| | | | |
|---|---|---|---|
| 9,914,458 B2* | 3/2018 | Sato | G08G 1/096791 |
| 10,241,206 B2* | 3/2019 | Pink | G01S 17/931 |
| 10,265,035 B2* | 4/2019 | Fehre | A61B 6/4441 |
| 10,324,170 B1* | 6/2019 | Engberg, Jr. | G01S 7/4818 |
| 10,442,435 B2* | 10/2019 | Luo | B60W 60/0016 |
| 10,451,716 B2* | 10/2019 | Hughes | G05D 1/0061 |
| 10,674,979 B2* | 6/2020 | Fehre | A61B 6/4441 |
| 10,698,415 B2* | 6/2020 | Indrakanti | H04N 23/90 |
| 10,773,717 B2* | 9/2020 | Guibert De Bruet | H04N 23/60 |
| 10,793,123 B2* | 10/2020 | Zhou | B60T 8/171 |
| 10,925,564 B2* | 2/2021 | Vija | A61B 6/467 |
| 11,016,181 B2 | 5/2021 | Schwarz | G01S 7/4817 |
| 11,079,764 B2* | 8/2021 | Nister | G05D 1/0242 |
| 11,213,263 B2* | 1/2022 | Agrahari | A61B 6/102 |
| 11,517,282 B2* | 12/2022 | Dickmann | A61B 6/4405 |
| 11,690,582 B2* | 7/2023 | Kumar | A61B 6/56 378/198 |
| 11,708,088 B2* | 7/2023 | Liu | G01C 21/38 701/26 |
| 11,712,210 B2* | 8/2023 | Dencovski | A61B 6/102 378/198 |
| 11,884,295 B2* | 1/2024 | Shin | B60W 30/09 |
| 2017/0347979 A1 | 12/2017 | Fehre | |
| 2018/0279981 A1 | 10/2018 | Fehre et al. | |
| 2020/0253570 A1 | 8/2020 | Agrahari et al. | |
| 2020/0405256 A1 | 12/2020 | Dickmann et al. | |
| 2021/0219927 A1 | 7/2021 | Dencovski | |

FOREIGN PATENT DOCUMENTS

| | | |
|---|---|---|
| DE | 102016204618 A1 | 9/2017 |
| DE | 102016209576 A1 | 12/2017 |
| DE | 102019209543 A1 | 9/2020 |
| KR | 100422627 B1 | 3/2004 |
| WO | 2021072380 A1 | 4/2021 |

* cited by examiner

MOBILE MEDICAL DEVICE INCLUDING A LIDAR SENSOR AND A METHOD FOR CONTROLLING SUCH A MOBILE MEDICAL DEVICE

The present patent document claims the benefit of German Patent Application No. 10 2021 210 771.0, filed Sep. 27, 2021, which is hereby incorporated by reference in its entirety.

TECHNICAL FIELD

The disclosure relates to a method for the automatic control of a drivable, mobile medical device and an apparatus for performing such a method.

BACKGROUND

The term "a mobile X-ray device" refers to an X-ray device that may be used in a mobile manner, in particular is drivable on the ground, and the X-ray device may be used, for example, in different rooms of a clinic. Mobile X-ray devices may be arranged on equipment trolleys having wheels or rollers and may be manually pushed or moved. Mobile X-ray devices which are arranged on motorized equipment trolleys have a particularly large degree of flexibility with regard to how they are used in different areas or rooms. Such mobile X-ray devices are known, for example, from DE 10 2015 218 922 A1. It is intended in future to also use self-driving, motorized mobile X-ray devices.

In order to be transported between operating theaters or for other transfer moves, such self-driving mobile X-ray devices require a fast travel mode which allows the device to travel at the speeds of a quick pedestrian (e.g., $$5 \frac{km}{h}$$

This travel mode is quicker than the movements previously provided in the operating theater (e.g., $$25 \frac{cm}{s} = 0.9 \frac{km}{h}$$

A combination of power (power-assisted, motorized travel) and mass (e.g., 500 kg) requires a first-time-failure safe system for avoiding collisions. In the case of mobile C-arms, collision avoiding systems are known for the movements of the receiving system and the collision avoiding systems have, for example, a capacitive sensor system on the C-arm or flat detector. Such a sensor system has not yet been integrated for movements of the chassis/equipment trolley. In order to meet the necessary safety requirements, known mobile medical devices have an integrated speed limitation (both of the devices itself and also of the other where appropriate motorized axles, such as an axle for orbital movements, for angular movements and a stroke axis) and a tactile sensor system for collision recognition.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object of the present disclosure is to provide a method which renders it possible for an in particular autonomous drivable, mobile medical device to avoid collisions in a first-time-failure safe manner. Furthermore, the object of the disclosure is to provide a mobile device that is suitable for performing the method.

The object is achieved by a method for controlling a drivable, mobile medical device having a collision control system that has at least one LiDAR sensor; a method for the automatic control of at least of one drivable, mobile medical device in the surroundings of a static unit having a collision control system that has at least one LiDAR sensor; a mobile medical device; and an entire system.

The method for the automatic control of a drivable, mobile medical device having a collision control system that has at least one LiDAR sensor includes automatic (e.g., autonomously controlled via drives) or manually assisted (e.g., pushed) locomotion of the device at a first speed. The method further includes periodic joint scanning of at least one part of the surroundings of the device and a device section that is specified and arranged permanently fixed on the device, using the at least one LiDAR sensor during the locomotion, evaluation of the scan data of the surroundings, the scan data being recorded by the LiDAR sensor, to the effect that a section of the surroundings that is located in the travel direction of the device is checked for objects. The method further includes evaluation of the scan data of the specified device section, the scan data being recorded by the LiDAR sensor, in such a manner that a functional capability of the LiDAR sensor is tested and control of the speed of the device in a closed-loop manner depending on the result of the evaluations.

Light detection and ranging (LiDAR) sensors are known. LiDAR sensors may scan their surroundings, for example, horizontally with a laser beam over a determined angular segment (up to 360°) and as a result generate a high-resolution 2-D map of the surroundings. The main function of LiDAR sensors is to measure the distance between themselves and objects in their field of view. For this purpose, the time is used which a light pulse requires to travel the distance from the sensor to the object and back. Scanning may be carried out, for example, by a rotating mirror onto which the laser light is directed.

By a skillful conversion, an expedient sensitive area in the form of a rectangle or any polygon may be created from the scanned circular sensitive area. This may be done, for example, in coordination with a determination of the direction of travel of a device, so that objects may be detected in a rectangular/polygonal area in the travel direction. For the shape of the monitoring area, upcoming changes in travel direction in particular may be included (analogous to unequal illumination when negotiating bends, cornering light).

Scanning is repeated periodically, during each scanning cycle evaluations are performed on the surroundings and the functional capability, and appropriate closed-loop controls are performed. This is continued, in particular, as long as the mobile medical device is moving along.

In addition, the disclosure includes a mobile medical device having an equipment trolley, wherein the equipment trolley has motorized wheels and a control unit for controlling the motorized wheels and a collision control system. The collision control system having at least one LiDAR sensor arranged in such a manner that the sensor scans at least one part of the surroundings of the equipment trolley and a device section. The mobile medical device further includes a processing unit configured to process and evaluate scan data, which is recorded by the LiDAR sensor, with respect to a detection of objects in the travel direction of the device trolley and with respect to a functional capability of the LiDAR sensor. The mobile medical device further includes a closed-loop control unit configured to control the speed of the device in a closed loop manner depending on the result of the evaluation.

It is possible using the method or the mobile medical device and using a LiDAR sensor to detect in a simple and rapid manner an object which appears in the planned travel path of the device and to initiate an appropriate measure so as to avoid a collision. As a result, it is possible to avoid accidents and the device may be configured to be collision-proof. By virtue of the fact that the LiDAR sensor is arranged in such a manner that it may also perform a self-test, the requirement for first-time-failure safety of the mobile medical device is fulfilled. At the same time, it is possible in a simple manner using the same simple sensor system, (e.g., the LiDAR sensor), for continuous self-testing of the device to be performed and for objects in the travel path to be detected. In addition, it is thus possible to avoid collisions occurring again as a result of errors or a malfunction of the sensor system. The method renders possible maximum safety of the device. The equipping of a mobile medical device with such a collision control system having a LiDAR sensor is cost-effective and it may be performed in a simple manner with simultaneous high safety.

The self-test is performed in such a manner that the LiDAR sensor scans the device section that is specified and known during each scanning cycle and the evaluation recognizes as soon as a deviation occurs here. By virtue of the fact that device sections which are always known are to be detected in the monitoring area, the correct function of the LiDAR sensor may be tested at any point in time and consequently a high safety standard is met.

In addition to an appropriate arrangement of the at least one LiDAR sensor on the mobile medical device, it is also possible to provide that the LiDAR sensor is arranged on a static unit and from there to monitor an approach of the at least one drivable medical device.

According to one embodiment, the specified device section includes at least one wheel, e.g., two or more wheels. The LiDAR sensor may also be arranged, for example, on an underside of the equipment trolley in such a manner that when a scan is performed over, for example, 180°, 270°, or 360°, two of the wheels of the equipment trolley are included in the scan, when a scan is performed over 360°, it is possible to include all four wheels in the scan. Such an arrangement of the LiDAR sensor is possible with a small outlay, the monitoring area in the travel direction may be particularly easily scanned by the LiDAR sensor and the wheels are used for the self-test. In the case of a 360° scan, it is possible in a reliable manner to monitor all possible travel directions (in other words, for example, forwards, backwards, sideways etc.), because the entire surroundings are scanned, and the travel direction may be included.

According to a further embodiment, the mobile medical device is configured to be autonomously drivable and is activated for automatic locomotion. Such a device does not require manually assisted locomotion (e.g., pushing) by an operating person. Instead, such a device may be controlled, moved, or driven automatically, for example, by a control unit. Such autonomously drivable devices may be used in future in clinics and hospitals on account of their flexibility. The method for collision control is particularly suitable for such mobile medical devices and assists their autonomous locomotion by additional safety.

According to a further embodiment, the speed of the device is automatically reduced or decelerated, or the device is stopped when the evaluation of the scan data of the surroundings indicates that an object has been detected in the travel direction, e.g., in a rectangular monitoring area in the travel direction. In this case, it is possible, for example, to activate brakes which in the case of autonomously driving devices results in a reduction of the speed. In the case of devices that are being pushed, it is possible to activate a speed limitation which makes it impossible for the device to move quicker. The device may also be completely stopped. The speed may be reduced at least to such an extent that, in the event of a collision with the detected object, it is not possible for damage or injury (to a person) to occur.

According to a further embodiment, the speed of the device is automatically reduced or decelerated, or the device is stopped when the evaluation of the scan data of the device section indicates a limited functional capability of the LiDAR sensor. If, in other words, the evaluation during the detection of the known device section detects a deviation, for example, or it is not possible to perform a detection/evaluation, it is possible for safety reasons for the device to initiate a stop or an appropriate reduction in speed.

According to a further embodiment, the maximum speed of the device achievable for the automatic or manually assisted locomotion of the device is configured in such a manner that at least one of the following conditions is fulfilled: the braking distance at maximum speed is at the most as large as the maximum possible scanning distance and/or the maximum speed is at the most as large as the maximum possible scanning distance per scanning cycle duration.

If the braking distance at maximum speed is at the most as large as the maximum possible scanning distance, this means that the device may come to a standstill within the last scanned or evaluated area. This is important so that a collision does not occur when an object appears. Depending upon the design of the mobile device (in other words depending upon how large the maximum possible scanning distance and the braking force are), it is then possible to limit the maximum speed of the mobile device. In the case of an autonomously driving device, the maximum speed may refer to the speed which the device may maximally drive itself or, in the case of a manually assisted drivable device, the maximum speed may refer to the speed which the device may maximally achieve by being pushed (with greater force it is possible, for example, to decelerate the device).

In addition, it is still possible to include the evaluation time with the result that the maximum speed may be limited to a greater extent.

According to a further embodiment, the open-loop control unit and closed-loop control unit are formed by a system controller which controls, for example, the mobile device or the entire system. The system controller receives for this purpose the relevant information via the evaluations.

In particular, the closed-loop control unit (e.g., system controller) of the medical device is configured, in the event that an object is detected in the travel direction, to trigger a reduction in the speed of the device and/or a deceleration.

In an advantageous manner, the mobile medical device is formed by an imaging device, e.g., a mobile X-ray device having a C-arm or a mobile CT. For example, mobile C-arm X-ray devices are frequently used in clinics and hospitals in order to be moved flexibly into different rooms and to create images of organs and body parts for a rapid diagnosis. With the aid of the disclosure, it is possible to increase the speed and safety of the transport of such devices.

According to a further embodiment, two or more LiDAR sensors may also be arranged on the mobile device. It is thus possible to monitor, for example, different travel directions (e.g., forwards, backwards, sideways) using different LiDAR sensors which then do not monitor, for example, 360° but monitor, for example, only a 90° angular segment. Depending upon the travel direction, it is possible for this purpose, for example, to switch on the relevant LiDAR sensor.

The inclusion of the travel direction may be registered, for example, by the system controller or by further sensors and compensated using the LiDAR sensor or the evaluation unit.

BRIEF DESCRIPTION OF THE DRAWINGS

The disclosure is further explained below with aid of exemplary embodiments schematically illustrated in the drawings, without thereby limiting the disclosure to these exemplary embodiments. In the drawings.

DETAILED DESCRIPTION

Figure 2:
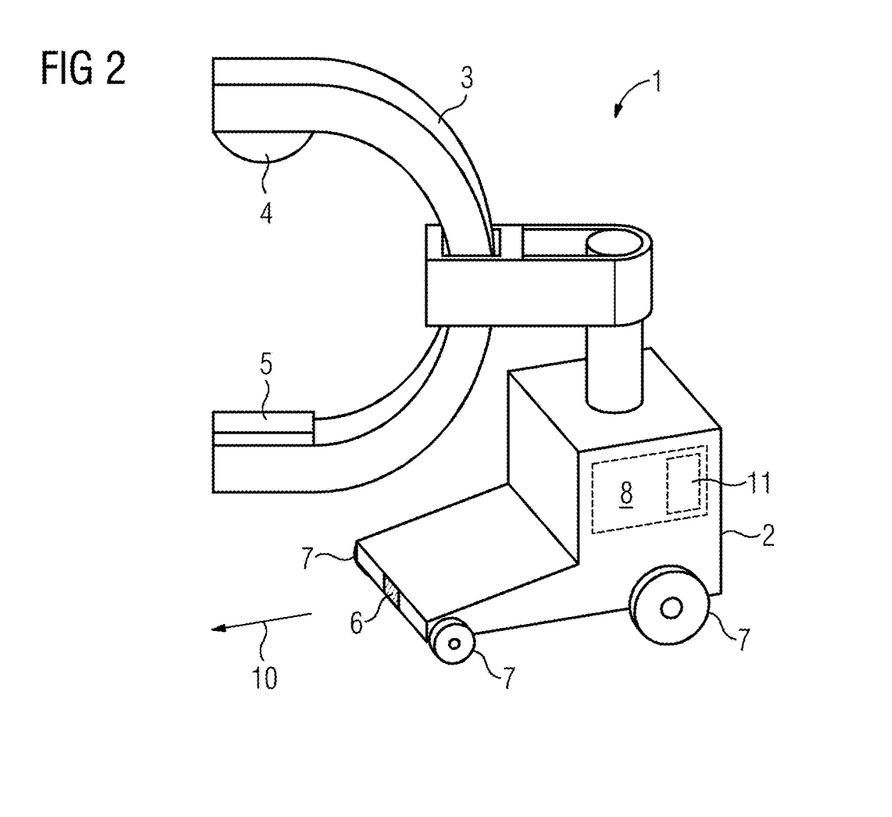
FIG. 2 depicts a view of an example of a mobile X-ray device having a LiDAR sensor for performing the method.

FIG. 2 shows a mobile medical device having a LiDAR sensor 6. The device in the example is a mobile C-arm X-ray device 1, which has an equipment trolley 2 and a C-arm 3 having an X-ray source 4 and an X-ray detector 5. The equipment trolley 2 includes motorized wheels 7 for the locomotion, (e.g., four wheels of which two are front wheels and two are rear wheels). The wheels 7 of the mobile device 1 may have one or more drives and may be decelerated by brakes or by the respective drive.

The mobile C-arm X-ray device 1 has a system controller 8 by which the device may be controlled. The motorized wheels 7 may also be controlled for locomotion or deceleration. The C-arm X-ray device 1 that is shown as an example is configured for autonomous locomotion. However, the disclosure may also include manually assisted drivable, (e.g., pushable), devices (see below). A LiDAR sensor 6 is arranged on the underside of the equipment trolley 2, for example, between the two front wheels 7. The LiDAR sensor 6 may have a form with a rotatable mirror onto which laser light is transmitted. The mirror rotates in a scanning cycle in such a manner that, for example, an angular segment of at least 180° (e.g., 180°, 270°, or a complete circle K, in other words) 360° is scanned. The resolution may be configured in this case, for example, in degrees or sub-degree increments.

Figure 3:
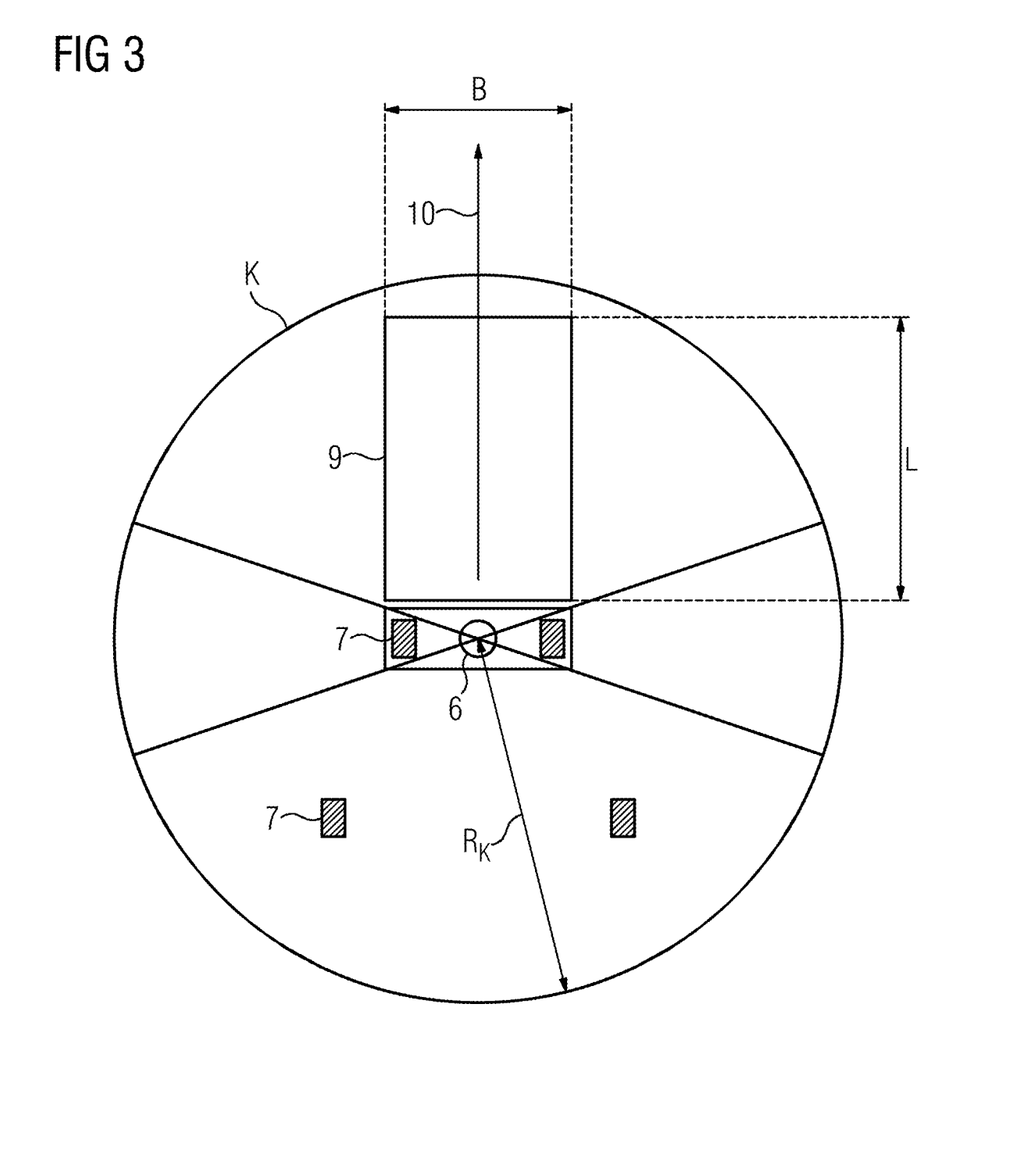
FIG. 3 depicts a plan view of an example of the sensitive areas of the LiDAR sensor being used.

FIG. 3 shows so as to explain the scanned area a 360° circle K and the LiDAR sensor 6 is arranged in its middle point. Furthermore, the wheels 7 are shown which, when the LiDAR sensor 6 is arranged on the lower side of the equipment trolley 2, are included in the scanning as a fixed device section. Using an appropriate calculation by the evaluation unit 11 (e.g., micro-controller), it is possible, from the scan data of a scanning cycle, in other words, from the scanned circular or segment-shaped sensitive area, to create an expedient sensitive area in the form of a rectangle 9 or any polygon in the travel direction 10 of the mobile device. The rectangle 9 may have a width B and a length L in the travel direction, wherein $L \leq R_K$ ($R_K$ is the radius of the scannable circle K), with the result that the length L forms a uniform smallest monitoring distance in the travel direction 10. In the example shown, the travel direction 10 is forwards, however, it is also possible to evaluate backwards, sideways, or other travel directions. This may be performed by the evaluation unit 11 if the unit receives the relevant information regarding the travel direction 10 (relative to the device), for example, from the system controller 8. The sensitive rectangle 9 may then, if necessary, be determined configured to the respective travel direction.

Figure 1:
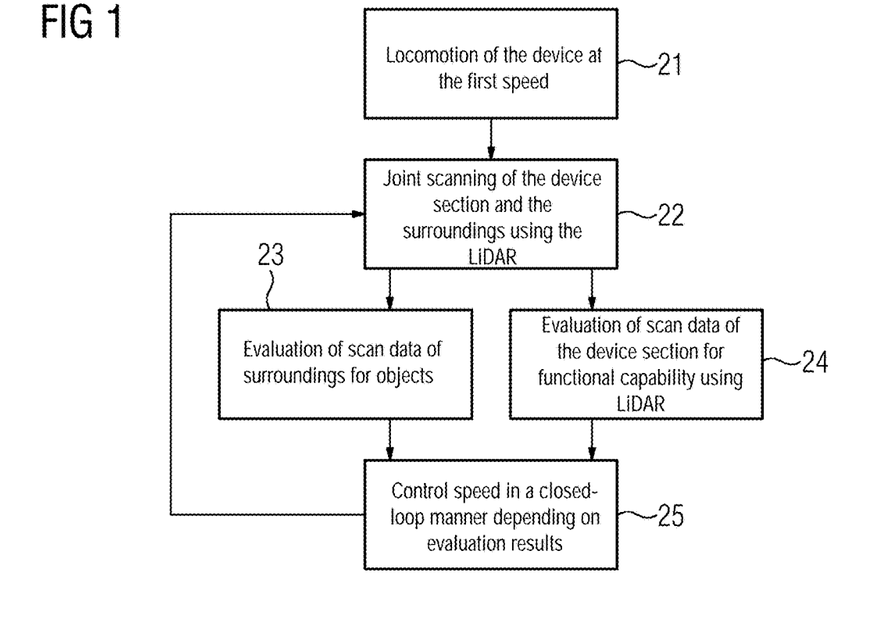
FIG. 1 depicts an example of a sequence of acts of a method for the automatic control of a drivable, mobile medical device.

FIG. 1 shows a sequence of acts of a method. In act 21, locomotion of the mobile device, (e.g., the mobile X-ray device 1), is initialized at a first speed. For this purpose, the mobile device 1 may be activated either automatically, in other words, for example, by a control command of the system controller 8, or by a user. The locomotion may be automatic, (e.g., instigated by the system controller 8), or manually assisted by a user, (e.g., pushed).

During the locomotion of the mobile device 1, at least one part of the surroundings of the device and a device section that is specified and arranged permanently fixed on the device are periodically jointly scanned in act 22 by the at least one LiDAR sensor. In each scanning cycle, a 180°, 270°, or 360° circle (segment) may be scanned and, for example, one or more wheels 7 or wheel claddings or a part of the housing of the mobile device. The scanning cycles are continued at least until the mobile device is no longer moving or is deactivated or until a control command to abort the collision monitoring is input.

The scan data of the LiDAR sensor 6 of each scanning cycle is evaluated immediately.

In act 23, for each scanning cycle the recorded scan data of the surroundings is evaluated as to whether one (or more) object(s) has been detected in the travel direction of the device within a section (e.g., the rectangle 9) that is located there. If an object is detected, then this means that a collision is imminent. The evaluation is performed by a suitable evaluation unit 11, for example, a micro-controller.

In act 24, the recorded scan data of the specified device section (in other words, for example, wheels or wheel housing) is evaluated to the effect that a functional capability of the LiDAR sensor 6 is tested (e.g., self-test). It is important here that the device section remains the same so that the scan data has a value that is to be expected. If a deviation from this value occurs outside a tolerance range, then it is possible to assume that the function of the LiDAR sensor 6 is disrupted. The evaluation is performed by a suitable evaluation unit 11, for example, a micro-controller. One or more evaluation units 11 may be provided. Act 23 and act 24 may be performed in any sequence or also simultaneously.

Depending upon the evaluation results, the speed of the mobile device is controlled in a closed-loop manner in act 25. The scanning cycles including evaluation and closed-loop control are continued at least until the mobile device is no longer moving or is deactivated or until a control command to abort the collision monitoring is input.

Figure 4:
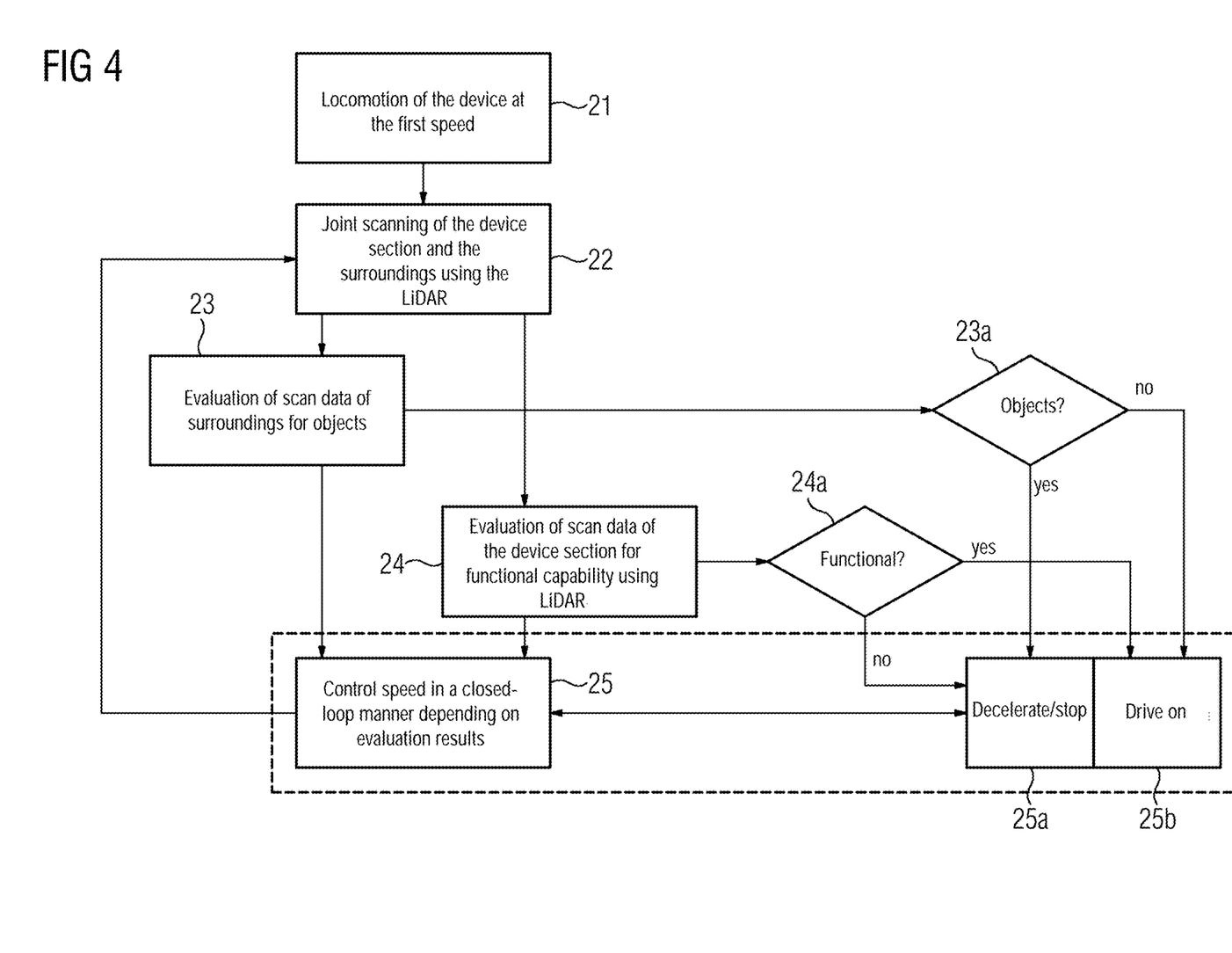
FIG. 4 depicts a further example of a sequence of acts of a method for the automatic control of a drivable, mobile medical device.

The closed-loop control of the speed of the mobile device is shown in detail in FIG. 4. Thus, if the evaluation in act 23 indicates that one or more objects have been detected 23a, a control command to decelerate or stop 25a the mobile device is issued. As a result, the mobile device may be stopped or decelerated to a lower speed. Likewise, if the evaluation in act 24 indicates a limited functional capability 24a, a control command to decelerate or stop 25a the mobile device is issued. As a result, the mobile device may likewise be stopped or decelerated to a lower speed. The reduced speed may be selected, for example, in such a manner that damage to the device is avoided. It is also possible to initiate an emergency stop. If both the functional capability is provided and also an object is not detected, the mobile device continues to be driven 25b at the same (e.g., the first) speed.

In the case of a mobile device that is driven autonomously or automatically, deceleration or stopping is automatically controlled and performed. In the case of a device that is manually pushed, the device may be decelerated, against the resistance of the push, to the appropriate lower speed or stopped or, for example, a speed lock is activated. The person pushing the device then feels the resistance. In addition, it is possible for a display or a warning sound to be activated.

The method renders it possible to reliably fulfill the necessary requirements with regard to first-time-failure safety of the mobile device. The described collision control system is both collision-proof and also functionally safe in accordance with risk analysis.

Overall, one or more conditions may apply for locomotion of the mobile device. It is, for example, important that the mobile device may come to a standstill within the last scanned area. It is possible to prescribe that the achievable or maximum adjustable maximum speed of the device meets at least one of the following requirements: the braking distance in the case of the maximum speed is at the most as large as the maximum possible scanning distance (e.g., the radius $R_K$ of the circle K or length L), and/or the maximum speed of the device is at the most as large as the maximum possible scanning distance (e.g., radius $R_K$ of the circle K or length L) per scanning cycle duration (e.g., duration of a scanning cycle, possibly plus evaluation). In addition, the evaluation durations may also be taken into consideration with the result that the maximum speed may be limited to an even greater extent. In order to meet the requirements, it is possible to provide a maximum speed lock.

An embodiment of a mobile medical device having at least one LiDAR sensor is cost-effective and safe. It is not necessary to provide hardware, which is itself fail-safe, because the integrity of the simpler hardware (appropriately positioned LiDAR sensor having an evaluation unit and a closed-loop control of the speed) is validated in real time (in relation to the multiple occurrence probability). A malfunction (deviation during the self-test) leads immediately to a removal of the degree of freedom that has been validated via the LiDAR sensor (e.g., distance, speed, etc.). In this manner, it is possible to also use simple positioning systems for safety-relevant functions.

Figure 5:
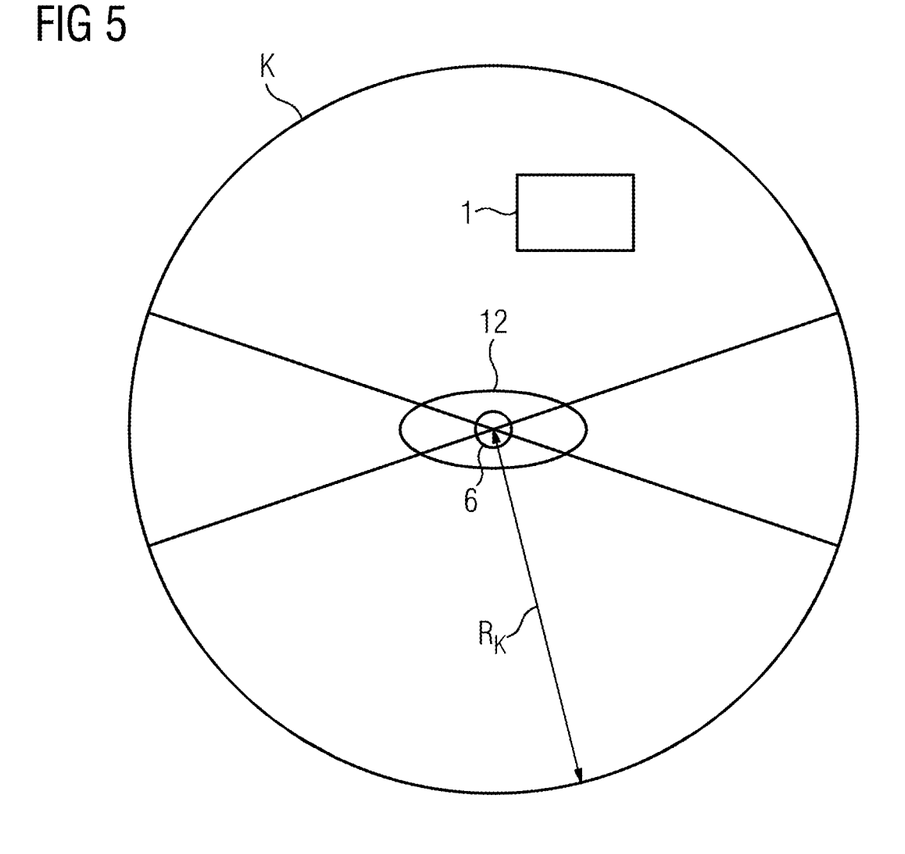
FIG. 5 depicts a view of an example of an entire system having a static unit having a LiDAR sensor and a mobile device in its surroundings.

As an alternative to a mobile device having a collision control system having a LiDAR sensor, it is also possible to arrange the collision control system having a LiDAR sensor on a static unit 12 and to control a mobile device 1 in the surroundings of the static unit 12—see FIG. 5. The LiDAR sensor 6 is arranged on the static unit in such a manner that it scans for example a 180°, 270° or 360° circle (segment) according to one or more mobile devices 1 and simultaneously in each scanning cycle also scans a fixed section on the static unit for a self-test. The scan data is then evaluated, and the speed of the mobile device or mobile devices is accordingly controlled in a closed-loop manner as described above. Additionally, communication between the static unit (e.g., the collision control system) and the mobile device is then required in order to determine which mobile device is located in the surroundings of the static unit, because the LiDAR sensor merely fundamentally detects objects.

The disclosure may be summarized in short as follows. For a first-time-failure safe movement of a mobile medical device, (e.g., a mobile C-arm X-ray device), a method is provided for the automatic control of a drivable, mobile medical device having a collision control system that has at least one LiDAR sensor. The method includes: automatic or manually assisted locomotion of the device at a first speed; periodic joint scanning of at least one part of the surroundings of the device and from a device section that is specified and arranged permanently fixed on the device, using the at least one LiDAR sensor during the locomotion of the device; evaluation of the scan data of the surroundings, the scan data being recorded by the LiDAR sensor, to the effect that a section of the surroundings that is located in the travel direction of the device is checked for objects; and evaluation of the scan data of the specified device section, the scan data being recorded by the LiDAR sensor in such a manner that a functional capability of the LiDAR sensor is tested and the speed of the device is controlled in a closed-loop manner depending on the result of the evaluations.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the embodiments, the disclosure is not limited to the disclosed examples. Other variations may be deduced by those skilled in the art without leaving the scope of protection of the claimed disclosure.

The invention claimed is:

1. A method for an automatic control of a mobile medical device having a collision control system comprising at least one LiDAR sensor, the method comprising:
   moving, automatically or manually, the mobile medical device at a first speed along a travel direction;
   periodic joint scanning, using the at least one LiDAR sensor during the moving of the mobile medical device, at least one part of surroundings of the mobile medical device and a specified device section arranged permanently fixed on the mobile medical device;
   evaluating scan data of the surroundings, the scan data of the surroundings being recorded by the at least one LiDAR sensor, such that a section of the surroundings located in the travel direction of the mobile medical device is checked for objects;
   evaluating the scan data of the specified device section, the scan data of the specified device section being recorded by the at least one LiDAR sensor, such that a functional capability of the at least one LiDAR sensor is tested; and controlling a speed of the mobile medical device in a closed-loop manner depending on a result of the evaluating of the scan data of the surroundings and the evaluating of the scan data of the specified device section.

2. The method of claim 1, wherein the mobile medical device is configured to be autonomously drivable, and
wherein the mobile medical device is activated for an automatic locomotion.

3. The method of claim 1, wherein a speed of the mobile medical device is automatically reduced or decelerated, or the mobile medical device is stopped when the evaluating of the scan data of the surroundings indicates that an object has been detected in the travel direction.

4. The method of claim 1, wherein a speed of the mobile medical device is automatically reduced or decelerated, or the mobile medical device is stopped when the evaluating of the scan data of the specified device section indicates a limited functional capability of the at least one LiDAR sensor.

5. The method of claim 1, wherein a maximum speed for the mobile medical device is configured such that:
a braking distance at the maximum speed is at most as large as a maximum possible scanning distance, and/or
the maximum speed is at most as large as the maximum possible scanning distance per scanning cycle duration.

6. The method of claim 1, wherein the at least one LiDAR sensor is configured for scanning an angular segment of at least 270°.

7. The method of claim 6, wherein the at least one LiDAR sensor is configured for scanning the angular segment of 360°.

8. The method of claim 1, wherein the specified device section comprises at least one wheel.

9. The method of claim 1, wherein the specified device section comprises two or more wheels.

10. A method for an automatic control of a mobile medical device in a surrounding of a static unit comprising a collision control system having at least one LiDAR sensor, the method comprising:
moving the mobile medical device at a first speed;
periodic joint scanning, using the at least one LiDAR sensor, at least one part of the surroundings of the static unit and a specified device section arranged permanently fixed on the static unit, during the moving of the mobile medical device at the first speed;
evaluating scan data of the surroundings of the static unit, the scan data of the surroundings of the static unit being recorded by the at least one LiDAR sensor, such that a section of the surroundings of the static unit is checked as to whether anything is approaching the mobile medical device;
evaluating scan data of the specified device section, the scan data of the specified device section being recorded by the at least one LiDAR sensor, such that a functional capability of the at least one LiDAR sensor is tested; and
controlling a speed of the mobile medical device in a closed-loop manner depending on a result of evaluations of the scan data of the surroundings of the static unit and the scan data of the specified device section.

11. A mobile medical device comprising:
an equipment trolley having motorized wheels;
a controller configured to control the motorized wheels; and
a collision control system having at least one LiDAR sensor arranged in such a manner that the at least one LiDAR sensor is configured to scan at least one part of a surrounding of the equipment trolley and a device section,
wherein the controller is further configured to process and evaluate scan data recorded by the at least one LiDAR sensor with respect to a detection of objects in a travel direction of the equipment trolley and with respect to a functional capability of the at least one LiDAR sensor, and
wherein the controller is further configured to control a speed of the mobile medical device in a closed-loop manner depending on a result of an evaluation of the scan data.

12. The mobile medical device of claim 11, wherein the mobile medical device further comprises an imaging device.

13. The mobile medical device of claim 12, wherein the imaging device is a mobile X-ray device.

14. The mobile medical device of claim 11, wherein the controller is further configured to initiate a reduction of the speed of the mobile medical device, and/or to initiate a deceleration of the mobile medical device when an object is detected by the at least one LiDAR sensor in the travel direction.

15. The mobile medical device of claim 11, wherein the controller is further configured to control an autonomous locomotion of the mobile medical device.

16. The mobile medical device of claim 11, wherein the at least one LiDAR sensor comprises two or more LiDAR sensors.

17. A system comprising:
a static unit has a collision control system comprising at least one LiDAR sensor arranged in such a manner that the at least one LiDAR sensor is configured to scan at least one part of a surrounding of the static unit and a section of the static unit; and
a mobile medical device having:
an equipment trolley comprising motorized wheels; and
a controller for controlling the motorized wheels,
wherein the controller of the mobile medical device is configured to evaluate scan data recorded by the at least one LiDAR sensor with respect to a detection of the mobile medical device and with respect to a functional capability of the at least one LiDAR sensor, and
wherein the controller of the mobile medical device is further configured to control a speed of the mobile medical device in a closed-loop manner depending on a result of an evaluation of the scan data.

* * * * *